United States Patent [19]

Yamauchi et al.

[11] Patent Number: 4,727,161

[45] Date of Patent: Feb. 23, 1988

[54] PROCESS FOR THE PREPARATION OF INDOLES

[75] Inventors: Atsuyoshi Yamauchi, Naka; Seiya Iguchi, Mitaka; Yuzo Ono, Takaishi; Hiroshii Kimura, Kamakura; Satoshi Morita, Yokosuka, all of Japan

[73] Assignee: Mitsui Toatsu Chemicals, Incorporated, Tokyo, Japan

[21] Appl. No.: 798,919

[22] Filed: Nov. 15, 1985

[30] Foreign Application Priority Data

Nov. 19, 1984 [JP] Japan ................................ 59-242295
Nov. 20, 1984 [JP] Japan ................................ 59-243373

[51] Int. Cl.$^4$ ................. C07D 209/08; C07D 209/12; C07C 85/26
[52] U.S. Cl. ..................................... 548/508; 203/28; 564/437
[58] Field of Search .......................... 548/508; 203/28; 564/437

[56] References Cited

U.S. PATENT DOCUMENTS 3,845,072 10/1974 Romano et al. .................. 260/319.1

FOREIGN PATENT DOCUMENTS 69242 1/1983 European Pat. Off. ............ 548/508
36-16719 9/1961 Japan .
2123820 2/1984 United Kingdom ............... 548/508

OTHER PUBLICATIONS

Patent Abstracts of Japan, vol. 8, No. 178, C-238 (1615), (Aug. 16, 1984) Kudou et al.
Patent Abstracts of Japan, vol. 7, No. 108, C-165 (1253) (May 11, 1983) Honda.

*Primary Examiner*—Mary E. Ceperley
*Attorney, Agent, or Firm*—Fisher, Christen & Sabol

[57] ABSTRACT

A process for producing an indole which comprises reacting an aniline and a diol in the presence of a catalyst to produce a reaction mixture containing the indole, unreacted aniline and by-products, condensing the reaction mixture to obtain a liquid reaction product, recovering the unreacted aniline from the liquid reaction product, reducing the contents of specified by-products in the recovered aniline below specified levels and reutilizing the resulting recovered aniline. To reduce the contents of the specified by-products in the recovered aniline below specified levels, it is preferred to subject the liquid reaction product or an aniline fraction separated therefrom to a heat-treatment and then to distillation. In the above manner, the recovered aniline can be reutilized in the reaction without causing the activity of the catalyst to deteriorate.

4 Claims, No Drawings

PROCESS FOR THE PREPARATION OF INDOLES

BACKGROUND OF THE INVENTION (1) Field of the Invention

This invention relates to a preparation process of an indole from an aniline and a diol. More specifically, it relates to a process for preparing an indole by reacting an aniline with a diol in a vapor phase in the presence of a catalyst containing at least one element selected from Group Ib of the periodic table, wherein the unreacted aniline is separated from the indole, prior to, concurrently with or subsequent to being treated so as not to deteriorate the activity of the catalyst, and recycled to the reaction for its reutilization.

(2) Description of the Prior Art

Indoles are widely used as raw materials for the chemical industry such as perfumes, dyes and the like and especially, have lately been noted as a raw material for the synthesis of amino acids. Indoles have conventionally been prepared by the use of expensive raw materials or by way of long troublesome steps. However, there has recently been found a process for preparing an indole by using an aniline and a diol as economical raw materials and by way of simple steps.

As the catalyst for use in this reaction, a variety of solid acid catalysts and metallic, catalysts have been proposed. The present inventors have examined the reaction from various angles. As a result, it has become clear that a catalyst containing any one of Cu, Ag and Au, which are the elements of Group Ib of the periodic table, is effective for the reaction and that where an indole is synthesized from an aniline and a diol by using this catalyst, it is necessary to cause a large amount of the aniline to exist in the reaction system in order to obtain the indole in high yield. Therefore, where this catalyst is used to synthesize the indole, it is indispensable to separate and recover a large amount of the aniline contained in the reaction mixture and use it repeatedly as a raw material for the reaction.

When the reaction is effected while using repeatedly such recovered aniline for a long period of time, the catalyst will exhibit a reduction in its activity to a degree that depends on the type of catalyst and the reaction conditions, as as compared with the case in which are unused aniline is employed.

Specifically, even a catalyst, which is capable of maintaining its catalytic activity at a sufficiently high level over a period of hundreds of hours where the reaction is effected without recycling the recovered aniline, will exhibit a marked reduction in its catalytic activity when the reaction is carried out by feeding the recovered aniline while maintaining the other conditions entirely identical. The catalyst thus-lowered in its catalytic activity will have to be subjected to frequent regeneration treatments by heating it in an oxygen atmosphere. This regeneration treatment is troublesome and its excessive repetition may sometimes impair the economical efficiency of the process. The reason of the reduction of its catalytic activity has not been clarified in detail. However, since the catalyst can be regenerated and activated by conventional means, it is assumed as the main reason that certain organic substances are converted to carbonaceous materials under the reaction conditions to precipitate on the surface of the catalyst and cover its active sites. The reduction of the activity can be minimized by carrying out the reaction in an atmosphere of hydrogen or by adding water to the reaction system. However, their effects are not necessarily satisfactory. This leads to the assumption that the recovered aniline may contain substances which are poisonous to the catalyst.

The liquid reaction product obtained by condensing a gaseous reaction mixture withdrawn from a reactor contains an indole produced, water, an unreacted diol, an excess aniline and still further small amounts of various by-products. Although some of the by-products are separated and identified, a majority of them have not yet been clarified in their chemical structures, physico-chemical properties, etc. However, it is assumed that these unclarified by-products may involve substances which are recycled to the reactor without being removed from the recovered aniline and precipitate on the surface of the catalyst as carbonaceous materials, thereby causing the activity of the catalyst to deteriorate. These by-products are assumed to be the ones which are difficult to be separated from the recovered aniline by usual distillation, in view of the fact that the aniline recovered by distillation in a conventional manner exerts an adverse effect upon the activity of the catalyst.

SUMMARY OF THE INVENTION

An object of the present invention is to provide an industrial process for preparing an indole by reacting an aniline with a diol wherein the aniline used in a large amount as a raw material is recovered and reutilized in the reaction.

Another object of the present invention is to provide a process for preventing the activity of the catalyst from being lowered by reducing the contents of specified by-products below specified levels in the aniline recovered for its reutilization.

A further object of the present invention is to provide a process in which the recovered aniline can be used as a reaction raw material without exerting an adverse effect upon the activity of the catalyst by the efficient removal of by-products contained in the recovered aniline, the by-products being poisonous to the catalyst and difficult to be removed by distillation.

These objects of the present invention can be achieved by the undermentioned process:

In a process for preparing an indole which comprises reacting an aniline with a diol in the presence of a catalyst containing at least one element selected from Group Ib of the periodic table to produce the indol, separating and recovering the unreacted aniline from the indole by distillation or the like, and reutilizing the unreacted aniline in the reaction, the improvement characterized in that the aniline contains a compound represented by the general formula (I):

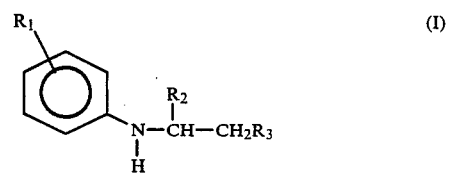

wherein $R_1$ represents a hydrogen atom, halogen atom, alkyl group, hydroxyl group, alkoxy group or nitro group and $R_2$ and $R_3$ are each a hydrogen atom, alkyl group or substituted alkyl group in an amount of 2% by weight or less, and a compound represented by the general formula (II):

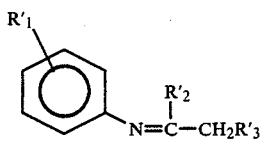
(II)

wherein $R_1'$ has the same meaning as $R_1$ in the general formula (I) and $R_2'$ and $R_3'$ have respectively the same meaning as $R_2$ and $R_3$ in the general formula (I) in an amount of 0.2% by weight or less.

According to the process of the present invention, a diol and an aniline in stoichiometrical excess of the diol are introduced into a reactor to produce a reaction product and then the excess aniline is separated and recovered from the reaction product for its reutilization as a raw material. Prior to its reutilization, the reaction product or the recovered aniline is subjected to a heat-treatment so as to convert by-products poisonous to the catalyst into non-volatile substances and thereby remove them by distillation or the like. Further, the recovered aniline can be used repeatedly while maintaining the activity of the catalyst at a high level by reducing the contents of by-products which impair the activity of the catalyst in the recovered aniline to certain specified levels as to render them harmless.

DETAILED DESCRIPTION OF THE INVENTION

An aniline useful in the process of the present invention is a compound of the general formula (III):

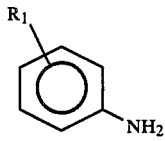
(III)

wherein $R_1$ represents a hydrogen atom, halogen atom, alkyl group, hydroxyl group, alkoxy group or nitro group. Specific examples thereof are aniline, o-, m- and p-toluidines, o-, m- and p-haloanilines, o-, m- and p-nitroanilines, o-, m- and p-hydroxyanilines, o-, m- and p-anisidines and the like.

On the other hand, a diol used in the process of the present invention is a compound represented by the general formula (IV):

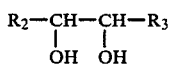
(IV)

wherein $R_2$ and $R_3$ are each a hydrogen atom, alkyl group or substituted alkyl group. Illustrative of such a diol may embrace ethylene glycol, propylene glycol, 1,2-butanediol, 2,3-butanediol, 1,2,4-butanetriol, and the like.

The catalyst which is used in the process of the present invention is a catalyst system containing at least one element selected from Group Ib of the periodic table, i.e., Cu, Ag and Au as effective components and besides, may optionally contain one or more other elements suitable for incorporation in combination with the above-mentioned effective components, for example, B, C, O, Mg, Al, Si, P, S, Ca, Ti, Cr, Mn, Fe, Co, Ni, Zn, Ga, Ge, Se, Sr, Zr, Mo, Ru, Rh, Pd, Cd, In, Sn, Sb, Te, Ba, La, Ce, W, Ir, Pt, Tl, Pb, Bi, Th and/or the like. The above-described catalyst components may be used singly or by supporting them on a conventional carrier such as diatomaceous earth, activated, clay, zeolite, silica, alumina, silica-alumina, titania, chromia, thoria, magnesia, calcium oxide, zinc oxide, and the like.

As regards the source of the Group Ib elements of the periodic table, when Cu and Ag are used as effective components, they may be employed as their nitrates, sulfates, phosphates, carbonates, halides, organic acid salts or the like. Where Au is used as an effective element, it may be employed as its chloroauric acid, alkali metal chloroaurate, gold cyanide, alkali metal cyanoaurate or the like.

As a preparation method of the catalyst, it is possible to follow the usual kneading method, co-precipitation method or impregnation method. Alternatively, two or more of these methods may be employed in combination. The catalyst may be prepared, for example, by mixing a variety of raw materials, adding a small amount of water and then kneading the resultant mixture in a kneader or the like; by forming various raw materials into an aqueous solution and then adding a precipitant to the aqueous solution to co-precipitate them as an insoluble precipitate; or by impregnating one of various carriers with various raw materials.

The catalyst composition thus-obtained is dried, usually, at temperatures below 180° C., added with a suitable pelletizing additive, forming assistant or the like and then formed. Alternatively, the catalyst composition may be used as it is only by crushing it.

In the process of the present invention, the reaction between an aniline and a diol is carried out in a vapor phase in the presence of the above-described catalyst. The reaction may be conducted by using any one of a fixed-bed, fluidized-bed or moving-bed reactor.

The amounts of an aniline and an diol fed to the reactor should be such that from 0.01 to 1 mole or preferably from 0.05 to 0.5 mole of the diol is provided for each mole of the aniline.

The feed aniline and diol are introduced, after being vaporized in advance in a vaporizer, into the reactor at a liquid hourly space velocity (LHSV) in the range of from 0.01 to 10 gram/hour.cc. At the same time, the feed materials may be accompanied by steam, hydrogen, carbon monoxide, carbon dioxide, methane, nitrogen, neon, argon or the like as their carrier gas. Of these carrier gases, steam, hydrogen and carbon monoxide are preferred because they are effective in prolonging the service life of the catalyst.

The reaction may be effected at a temperature in the range of from 200° to 600° C. and preferably from 250° to 500° C. Any of subatmospheric, atmospheric and superatmospheric pressures may be used as the reaction pressure, but atmospheric or superatmospheric pressure is preferred. Practically, it is preferable to use a pressure in the range of from $1.1 \times 10^5$ to $1.0 \times 10^7$ Pa, with the range from $2.0 \times 10^5$ to $5.0 \times 10^6$ Pa being more preferred.

In a process in which an indole is synthesized from an aniline and a diol, it is necessary to use the aniline stoichiometrically in excess of the diol and thus a gaseous reaction mixture withdrawn from the reactor is composed of the unreacted aniline, produced indole and by-products. The gaseous reaction mixture is condensed so as to produce a liquid reaction mixture containing the aniline, indole and by-products. The aniline is separated from the liquid reaction mixture by distillation.

When an aniline and a diol are reacted with each other in the presence of the foregoing catalyst, compounds represented by the above-described general formulae (I) and (II) are produced as by-products.

The compound represented by the general formula (I) is produced to the extent of from 0.01 to 1% by weight in the reaction mixture per once-through under the above-described indole-forming conditions. This compound has a boiling point close to that of the corresponding aniline. Therefore, when an aniline is recovered from the reaction mixture by distillation, this compound is distilled out together with the aniline depending on the distillation conditions so that it is accumulated in the reaction system by the repeated use of the aniline as a raw material for the reaction. Further, it is also difficult to isolate this compound from the corresponding aniline by crystallization or extraction.

Further, the compound represented by the general formula (II) is formed to the extent of from 0.01 to 2% by weight in the reaction mixture per once-through under the aforesaid indole-forming conditions. This compound is also relatively difficult to be separated from the aniline by means of distillation, crystallization, extraction or the like. Depending on the conditions employed in the separation, an aniline containing a high concentration of this compound may be circulated to the reaction system.

In the production of an indole as described above, the reutilization of an aniline which contains by-produced compounds represented by the general formulae (I) and (II) as they are will cause the yield of the indole to decrease or the reduction in the yield of the indole to accelerate along the passage of time.

However, if the contents of these compounds in an aniline used as a raw material are reduced below specified levels, it will be possible to prevent the activity of the catalyst from being deteriorated.

Specifically, it is advisable to use, as a raw material for the reaction, an aniline which contains the by-produced compound of the general formula (I) in an amount of 2% by weight or less and that of the general formula (II) in an amount of 0.2% by weight or less.

To reduce the contents of the compounds represented by the general formulae (I) and (II) in an recovered aniline to the foregoing levels, these compounds should be removed therefrom or converted to render them harmless by a treatment, prior to, concurrently with or subsequent to the separation of the aniline from the reaction mixture. The separation of these compounds from the aniline may be effected by a conventional separation technique such as distillation, adsorption or the like. The treating methods for rendering these compounds harmless may include those of reaction, heating, complex formation and the like, whereby these compounds may be converted into such substances that exert no adverse effects upon the indole synthesis reaction or that can be readily separated and removed from the reaction mixture or the recovered aniline. Particularly, by subjecting the liquid reaction mixture as it is or an aniline fraction removed with the indole from the liquid reaction mixture to a heat-treatment in the below-described manner, the compound of the general formula (II) is converted into a non-volatile substance so that it can be removed therefrom almost completely by distillation.

The temperature employed in the heat-treatment may be in the range of from 100° to 350° C. or preferably from 150° to 250° C. On the other side, the time for the heat-treatment may be so selected as to have sufficient duration to achieve the objects of the present invention depending on the treatment temperature. Generally, the duration of from 10 minutes to 10 hours is sufficient for this purpose.

The operating pressure of the heat-treatment is determined to be a pressure above the saturated vapor pressure of the solution to be treated, though it depends on the composition of the solution and the temperature of the treatment. The heat-treatment may be practiced in either a batch-wise or a continous manner. When treated in a continuous manner, the stream of the solution may be in any of such a state as complete mixing or plug flow, or in a flow state therebetween. However, a state closer to a plug flow may exhibit improved volume efficiency.

The by-products poisonous to the catalyst in the liquid reaction product or recovered aniline heat-treated as described above are converted by the heat-treatment into non-volatile substances which can therefore be separated and removed by conventional distillation. The thus-obtained aniline which contains the compounds of the general formulae (I) and (II) respectively in the aforementioned concentrations can be used repeatedly in the reaction as it is without any further treatment or by mixing it with a fresh unused aniline.

The process of the present invention will hereinafter be described more specifically by the following examples.

EXAMPLE 1

To a tubular reactor made of stainless steel and having an inner diameter of 20 mm, was packed 200 cc of a pellet-like catalyst comprising 13% by weight of silver supported on a $SiO_2$ tablet having a diameter of 3 mm and a thickness of 2.5 mm. To the tubular reactor through its inlet, were fed 300 g/hr of a raw material consisting of aniline which had not been used in the indole synthesis reaction (hereinafter referred to as unused aniline), ethylene glycol and water in a molar ratio of 12:1:8 and at the same time 30 Nl/hr of gaseous hydrogen to carry out the indole synthesis reaction. The reaction was effected at a temperature of 350° C. and a pressure of $5.0 \times 10^5$ Pa for 600 hours. The reaction product thus-obtained as subjected to oil-water separation to recover entirely a liquid phase consisting mainly of aniline and indole. The recovered liquid was distilled under a reduced pressure of 5 mmHg for about 150 hours by using a distillation apparatus provided with rectification part which comprises a packed column having an inner diameter of 100 mm and a height of 1,500 mm and packed with McMahon packing, thereby recovering 80 kg of aniline which contains substantially no N-ethylaniline nor acetaldehyde anil. This procedure was repeated twice to obtain 160 kg of aniline in total.

This recovered aniline was divided into seven lots, to six of which were added respectively 0.5, 1.0 and 3.0% by weight of N-ethylaniline and 0.02, 0.04 and 0.12% by weight of acetaldehyde, the remaining one lot being used as it is as a raw material for the reaction. 0.05, 0.09 and 0.29% by weight of acetaldehyde anil were respectively detected by gas chromatography from the lots which had been added with acetaldehyde.

The indole synthesis reactions were carried out using these lots of recovered aniline under the above-described reaction conditions. The results given in Table 1 were obtained.

TABLE 1

| Run No. | Amount of N—ethylaniline added (% by weight) | Content of acetaldehyde anil (% by weight) | Yield of indole[a] (%) 25 hours | 50 hours | 75 hours |
|---|---|---|---|---|---|
| 1 | None | None | 72 | 70 | 68 |
| 2 | 0.5 | None | 72 | 69 | 67 |
| 3 | 1.0 | None | 71 | 68 | 65 |
| 4 | 3.0 | None | 65 | 61 | 55 |
| 5 | None | 0.05 | 72 | 69 | 67 |
| 6 | None | 0.09 | 71 | 69 | 65 |
| 7 | None | 0.29 | 70 | 64 | 54 |

[a]Yield of indole based on ethylene glycol

EXAMPLE 2

The indole synthesis reaction was carried out under the same reaction conditions as described in Example 1 and aniline was recovered directly from the reaction product by using the same distillation apparatus described in Example 1. The aniline thus-recovered was added with unused aniline to supplement its shortage and recycled to the reactor as a raw material for the reaction.

The recycle of the recovered aniline to the reactor caused impurities to accumulate in the reaction sysyem. The concentrations of N-ethylaniline and acetaldehyde anil as measured by gas chromatography were 0.2% and 0.08% by weight respectively in the reaction raw material upon an elapsed reaction time of 1,000 hours. Then, the catalyst was changed to a new one to continue the above-described test. The results given in Table 2 were obtained.

COMPARATIVE EXAMPLE 1

The indole synthesis reaction was carried out under the same conditions as described in Example 2 except for using a distillation apparatus provided with a rectification part which comprises a packed column having an inner diameter of 100 mm and packed with a glass-made Raschig ring having a dimension of 5 mm$\phi \times$ 5 mm up to a height of 300 mm in the column. Upon an elapsed reaction time of 1,000 hours, the reaction raw material was analyzed by gas chromatography. The concentrations of N-ethylaniline and acetaldehyde anil were respectively 2.8% and 0.35% by weight in the reaction raw material. Then, the catalyst was changed to a new one to continue the above-described test. The results given in Table 2 were obtained.

TABLE 2

|  | Yield of indole[a] (%) | | |
|---|---|---|---|
|  | 25 hours after catalyst exchange | 50 hours after catalyst exchange | 75 hours after catalyst exchange |
| Example 2 | 72 | 69 | 67 |
| Comp. Example 1 | 61 | 55 | 50 |

[a]Yield of indole based on ethylene glycol

EXAMPLE 3

The indole synthesis reaction was practiced in the same manner as described in Example 2 except that a Cu-Cr catalyst (C-43, product of Toyo C.C.I. Co.) was used. Upon an elapsed reaction time of 1,000 hours, the reaction raw material was analyzed by gas chromatography. The concentrations of N-ethylaniline and acetaldehyde anil were respectively 0.3% and 0.10% by weight. Then, the catalyst was changed to a new one to continue the above-described test. The results given in Table 3 were obtained.

COMPARATIVE EXAMPLE 2

The indole synthesis reaction was carried out under the same conditions as described in Example 3 except for using a distillation apparatus equipped with a rectification part which comprises a packed column having an inner diameter of 100 mm and packed with a glass-made Raschig ring having a dimension of 5 mm$\phi \times$ 5 mm upto a height of 300 mm in the column. Upon an elapsed reaction time of 1,000 hours, the reaction raw material was analyzed by gas chromatography. The concentrations of N-ethylaniline and acetaldehyde anil were 3.5% and 0.4% by weight, respectively. Then, the catalyst was changed to a new one to continue the above-described test. The results given in Table 3 were obtained.

TABLE 3

|  | Yield of indole[a] (%) | | |
|---|---|---|---|
|  | 25 hours after catalyst exchange | 50 hours after catalyst exchange | 75 hours after catalyst exchange |
| Example 3 | 60 | 58 | 57 |
| Comp. Example 2 | 52 | 47 | 42 |

[a]Yield of indole based on ethylene glycol

REFERENCE EXAMPLE 1

The reaction was carried out for 800 hours under the same conditions as described in Example 1 except for using 200 cc of a pellet-like catalyst comprising 1.5% by weight of copper supported on a SiO$_2$ carrier having a diameter of 3 mm and a thickness of 2.5 mm. The reaction liquid thus-obtained was subjected to oil-water separation to obtain an organic liquid phase consisting mainly of aniline and indole.

The yield of indole based on ethylene glycol was 70.4% immediately after the initiation of the reaction. This yield gradually decreased along the passage of reaction time to 49.8% at 290th hour after the initiation of the reaction.

EXAMPLE 4

Approximately 100 kg of the organic liquid phase obtained in Reference Example 1 was fed to a stainless-steel stirring vessel equipped with a jacket for heating medium. The contents of the vessel were heated by a heating medium with moderate stirring. The interior temperature of the vessel was maintained for two hours after it had reached 200° C. Then, the organic liquid phase showed a vapor pressure of about 6 kg/cm.

Aniline was separated and recovered from the heat-treated liquid by distillation. Specifically, 25 kg of the organic liquid phase was fed to a distillation apparatus composed of a distillation still having an inner volume of 30 l, a packed column having an inner diameter of 80 mm and packed with a Raschig ring having a nominal size of ¼ inch upto a height of 2,000 mm, and a condenser. The organic liquid phase was subjected to batch distillation under the conditions of an operating pressure of 10 mmHg and a reflux ratio of 0.2. Subsequent to 0.4 kg of a first distillate, 20.3 kg of aniline fraction was distilled out. About 80 kg of recovered aniline was obtained by repeating the batch distillation in a similar manner.

Using this recovered aniline, the indole synthesis reaction was carried out in exactly the same manner as described in Reference Example 1. The yield of indole based on ethylene glycol was 70.7% immediately after the initiation of the reaction. The reaction was continued over a period of 320 hours. The yield at the end of this time period was measured to be 50.4% which was approximately of the same level as the reaction performance obtained in Reference Example 1. The concentrations of N-ethylaniline and acetaldehyde anil were respectively 0.5% and less than 0.01% by weight in the recovered aniline as measured by gas chromatography.

COMPARATIVE EXAMPLE 3

Approximately 100 kg of the organic liquid phase obtained in Reference Example 1 was directly subjected to batch distillation in the same manner as described in Example 4 without being submitted to the heat treatment in advance, thereby obtaining approximately 80 kg of recovered aniline.

Using this recovered aniline, the indole synthesis reaction was carried out in exactly the same manner as described in Example 1. The yield of indole based on ethylene glycol was 69.8% immediately after the initiation of the reaction. However, it dropped to 40.8% even at 120th hour after the initiation of the reaction. Although the concentration of N-ethylaniline in the recovered aniline was 0.5% by weight as measured by gas chromatography, which was not different from the result obtained in Example 4, the concentration of acetaldehyde anil was determined as high as 0.25% by weight.

What is claimed is:

1. A process for preventing a decrease in the yield of indole in an indole-forming process comprising:
    (a) reacting a stoichiometric excess of an aniline of formula (III):

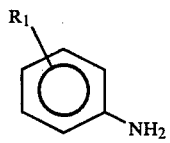
(III)

wherein $R_1$ is a hydrogen atom, a halogen atom, a lower alkyl group, a hydroxyl group, a lower alkoxy group or a nitro group, with a diol of formula (IV):

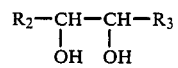
(IV)

wherein $R_2$ and $R_3$ are each a hydrogen atom or a lower alkyl group which may be substituted by a hydroxyl group, in the presence of a catalyst containing at least one element selected from Group Ib of the periodic table in the gas phase;
    (b) condensing the resultant gaseous reaction mixture to form a liquid mixture containing the indole, the excess aniline and compounds of formulas (I) and (II):

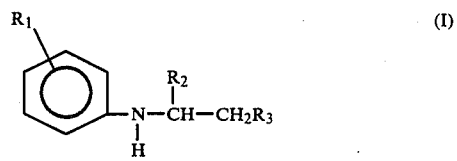
(I)

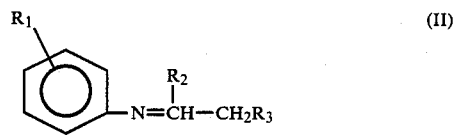
(II)

wherein $R_1$, $R_2$ and $R_3$ are defined as above;
    (c) separating the excess aniline from the liquid mixture;
    (d) subjecting the liquid mixture or the aniline separated to a heat-treatment to convert the compound of formula (II) into non-volatile substances;
    (e) subjecting the liquid mixture or aniline thus heat-treated to distillation to obtain the aniline containing not more than 2 percent by weight of the compound of formula (I) and not more than 0.2 percent by weight of the compound of formula (II); and
    (f) recycling the aniline from step (e) and using the aniline from step (e) in step (a); whereby reaction (a) is conducted without the reduction of activity of the catalyst.

2. A process as claimed in claim 1 wherein the aniline and diol are aniline and ethylene glycol, respectively, and the compounds of the formulas (I) and (II) are N-ethylaniline and acetaldehyde anil, respectively.

3. A process as claimed in claim 1 wherein the heat-treatment is carried out at a temperature of from 100° to 350° C.

4. A process as claimed in claim 1, wherein the heat-treatment is conducted for from 10 minutes to 10 hours.

* * * * *